United States Patent [19]

Kitajima

[11] 4,135,976

[45] Jan. 23, 1979

[54] TREATMENT OF PHOTOGRAPHIC PROCESSING EFFLUENTS USING PHOTOSYNTHETIC SULFUR BACTERIA

[75] Inventor: Masao Kitajima, Asaka, Japan

[73] Assignee: Fuji Photo Film Co., Ltd., Minami-ashigara, Japan

[21] Appl. No.: 776,556

[22] Filed: Mar. 10, 1977

[30] Foreign Application Priority Data

Mar. 11, 1976 [JP] Japan .................................. 51/26278
May 4, 1976 [JP] Japan .................................. 51/49848

[51] Int. Cl.² ......................... C02C 5/10; C22B 11/00
[52] U.S. Cl. .................................... 195/2; 75/101 R; 210/2; 75/118 P
[58] Field of Search ........................ 195/2; 210/2, 15; 75/101 R

[56] References Cited

U.S. PATENT DOCUMENTS

| | | | |
|---|---|---|---|
| 3,305,353 | 2/1967 | Duncan et al. .......................... | 195/2 |
| 3,455,679 | 7/1969 | Mayling .............................. | 75/101 R |
| 3,537,986 | 11/1970 | Watanabe et al. ...................... | 210/15 |
| 3,941,691 | 3/1976 | Romanenko et al. .................... | 210/2 |
| 4,033,763 | 7/1977 | Markels ................................ | 210/15 |

FOREIGN PATENT DOCUMENTS 12631 8/1970 Japan ......................................... 210/2

Primary Examiner—Lionel M. Shapiro
Attorney, Agent, or Firm—Sughrue, Rothwell, Mion, Zinn and Macpeak

[57] ABSTRACT

A process of treating a waste photographic processing solution containing reductive sulfur compounds, in particular, a waste fix solution for silver halide photographic materials, by applying thereto photosynthetic sulfur bacteria under anaerobic conditions with the irradiation of light. When the waste solution contains silver, the decontamination of the waste solution and the recovery of silver are performed simultaneously by the process.

18 Claims, No Drawings

TREATMENT OF PHOTOGRAPHIC PROCESSING EFFLUENTS USING PHOTOSYNTHETIC SULFUR BACTERIA

BACKGROUND OF THE INVENTION

1. Field of the Invention

The present invention relates to a process of purifying or decontaminating photographic processing effluents and recovering silver therefrom by applying photosynthetic sulfur bacteria to the photographic processing effluents. More particularly, the invention relates to a process of purifying or decontaminating photographic processing effluents containing reductive sulfur compounds, in particular, waste fix solutions for silver salt photographic materials, and recovering silver from such effluents or solutions separately or simultaneously by applying photosynthetic sulfur bacteria to these effluents or solutions under anaerobic conditions with light irradiation.

2. Description of the Prior Art

Many kinds of processing solutions for conventional silver halide photographic materials depending on the purpose of the processing are known but the most fundamental processing solutions for silver halide photographic materials are developers and fix solutions. A fix solution is an aqueous solution which is used for dissolving away silver halides present in silver halide photographic materials at the portions unexposed to light after development and a fix solution contains, as the main components, thiosulfates, sulfites, acetic acid, etc. Thus, a used fix solution contains the components described above in addition to solubilized silver thiosulfate complex salts. Consequently, in such a waste or used fix solution, the biological oxygen demand (BOD), the chemical oxygen demand (COD), and the total oxygen demand (TOD) which are indices showing the extent of contamination of waste solutions generally are very high. It is desirable to purify or decontaminate these waste fix solutions, that is, to reduce the above-described oxygen demands of waste fix solutions before these solutions are discharged in general. Of the above-described contaminants present in waste fix solutions, sulfur compounds represented, in particular, by thiosulfate ions ($S_2O_3^{--}$) are the main consumer of oxygen and the amount of these compounds present in waste solutions is large. Therefore, a great need for an appropriate treatment of these components exists.

On the other hand, a developer is a processing solution which is used for reducing silver halides in the portions exposed to light of silver halide photographic materials to silver and a developer is usually an alkaline aqueous solution mainly containing developing agents such as hydroquinones, p-aminophenols, phenylpyrazolidones, p-phenylenediamines, etc., together with sodium sulfite. Thus, a waste developer also has a high BOD, COD and TOD.

Examples of other photographic processing solutions are a bleach solution, a processing solution for removing silver from developed siver halide photographic materials, a neutralizing solution, washing water, etc.

SUMMARY OF THE INVENTION

This invention relates to a process of efficiently purifying or decontaminating waste solutions used for processing silver halide photographic materials, in particular, of reducing the oxygen demands of a waste fix solution or a mixture of a waste fix solution and another waste photographic processing solution or solutions by treating the solution or solutions with certain photosynthetic sulfur bacteria.

The invention is based on the discovery that certain photosynthetic sulfur bacteria are photosynthetically active, that is, they accomplish carbon dioxide assimilation and photophosphorylation in waste photographic processing solutions under the irradiation of light and anaerobic conditions to grow, proliferate, oxidize reductive sulfur compounds, and at the same time, acetic acid, carbonate ions, and ammonium ions in the solutions are consumed as the carbon source and nitrogen source, whereby these waste solutions can be purified or decontaminated, that is, the oxygen demands (COD, BOD, TOD) which are indices showing the decontamination extent of waste solutions can be reduced, and that the biological activity of the abovementioned photosynthetic sulfur bacteria is not hindered by the silver-thiosulfate complex salt present to a certain extent in waste photographic fix solutions under certain conditions.

Accordingly, the process of this invention provides a method of purifying a waste photographic processing solution containing sulfur compounds which comprises applying photosynthetic sulfur bacteria to the waste photographic processing solution under irradiation of light and anaerobic conditions.

DETAILED DESCRIPTION OF THE INVENTION

The term "photosynthetic sulfur bacteria", is used herein to describe microorganisms which are phototrophic and able to metabolize inorganic sulfur compounds, or more specifically they can be defined as microorganisms which are able to grow as anaerobes or aerotolerates in the light in mineral media containing inorganic sulfur compounds, bicarbonate and some simple organic substrates. Generally no organic growth factors are required but some species require Vitamin $B_{12}$.

In practice, application of photosynthetic sulfur bacteria to a waste photographic solution can be achieved in various ways; for example they can be admixed with the waste solution in a batch system or a continuous flow system, they can be supplied into the waste solution as a high concentration innoculum which has been cultivated separately or in a very diluted suspension to be cultivated to grow, proliferate etc. in the waste solution.

They can be applied as a column in which they are packed and stabilized so that a waste solution can be passed through the column so that the solution contact with the bacteria for a certain period of time during which the purification of the solution or accumulation of silver takes place.

They can be applied also as a fixed bed in which they are immobilized on a solid substrate and a waste solution is passed through the bed. In all these cases the photosynthetic sulfur bacteria can be applied either in their biologically active form, a state of cells in which the bacteria can grow or proliferate actively, or inactive form, a state of cells in which the bacteria can not grow or proliferate actively or are incapable of cell division.

A waste fix solution used in silver salt photography contains a large amount of silver dissolved therein from the unexposed portions of silver salt photographic materials in the form of silver-thiosulfate complex salts. Since silver itself is a very valuable metal, various attempts have hitherto been made for recovering silver from waste fix solutions (see "Recovering Silver from Photographic Materials" Kodak Publication No. J-10, 1972, Eastman Kodak Company, Rochester, N.Y.). For example, practically employed processes, include a process in which a wire gauze of a metal having a higher oxidation potential than that of silver, such as iron and aluminum, is placed in a waste fix solution and silver deposits thereon due to the difference in ionization tendency and the metallic silver thus deposited is recovered, a process in which metallic silver deposited on a cathode disposed in a waste fix solution is recovered by electrolysis, and a chemical process in which a reactant capable of forming a sparingly water-soluble compound or complex is added to a waste fix solution to recover silver as a precipitate of a silver salt or sodium borohydride is added to a waste fix solution to precipitate and recover silver as reduced silver. These processes, however, have both advantages and disadvantages and hence they can not always be utilized optimally under all circumstances.

That is, although the electrochemical process involving immersing a wire gauze of the metal is a process which can be easily practiced, the process must be carried out under conditions such that the concentration of silver-thiosulfate complex salt in the waste fix solution is comparatively high. Further, in the process the iron ions or aluminum ions dissolve into the waste solution by the replacement reaction with silver ions to contaminate the waste solution.

The electrolytic process may be a more desirable process but this process is less advantageous in the point of cost since the process needs additional appropriate equipment and further the process uses a large amount of electric power. A high concentration of silver thiosulfate complex salt is also required. Furthermore, it is necessary, in the electrolytic process, to attempt to utilize the equipment effectively by collecting large amounts of highly concentrated silver-containing waste solutions from each location where the fix solution is actually used.

The chemical process described above is accompanied by the possibility of a secondary contamination of the waste solution by the reactant added.

This invention also provides a process of recovering silver from a silver-containing waste fix solution by treating the waste solution with photosynthetic sulfur bacteria to capture and accumulate silver in the cells of the bacteria. The process of this invention has various advantages as compared with the above-described conventional silver recovery processes since the process of this invention can be applied to waste fix solutions containing a lower amount of silver salt than those to which the conventional processes are applicable and also the concentration of silver salt in the fix solution after treatment can be sufficiently reduced. However, the most excellent advantage of the process of this invention arises due to the following. By treating waste fix fix solutions with photosynthetic sulfur bacteria, the compounds which are present in the waste fix solutions and which are the cause of increased oxygen demands and BOD, COD, and TOD, such as sulfur compounds as well as ammonia, carboxylic acids, bicarbonate, carbonate, alcohols, etc., are consumed and digested by the photosynthetic sulfur bacteria as electron donors for the photosynthetic acitivity of the bacteria or the nutrients for growing the bacteria and thus the recovery of silver and the purifying of the waste solutions can be simulaneously performed.

As mentioned above, the invention provides a process of effectively purifying waste processing solutions or effluents used for processing silver halide photographic materials, in particular, waste fix solutions or a mixture of a waste fix solution and another waste photographic processing solution or solutions and the recovery of silver from these waste solutions by treating the waste solutions with photosynthetic sulfur bacteria.

The invention is described below in detail.

Photosynthetic sulfur bacteria are a kind of photosynthetic bacteria, which can grow under anaerobic conditions utilizing mainly reductive sulfur compounds as the sources of the reducing power required for carbon dioxide assimilation and photophosphorylation in the light. The reductive sulfur compounds which can be utilized as the electron donors for these photosynthetic sulfur bacteria differ depending on the kind of bacteria employed.

Sulfide ($S^{--}$) is effectively utilized by any photosynthetic sulfur bacteria and thiosulfate ($S_2O_3^{--}$), elementary sulfur (S), sulfite ($SO_3^{--}$), etc. are also utilized by some kinds of photosynthetic sulfur bacteria. In any cases where these sulfur compounds or sulfur is utilized as the electron donors for photosynthetic sulfur bacteria, the sulfur compounds or sulfur is finally oxidized to sulfate ($SO_4^{--}$) which is the highest oxidation state of sulfur. Photosynthetic sulfur bacteria which can effectively consume thiosulfate ($S_2O_3^{--}$) as the electron donors can be suitably used in this invention.

The metabolism of these reductive sulfur compounds by the photosynthetic sulfur bacteria has not yet been completely clarified but in the case of utilizing, for example, bacteria of the Genus *Chromatium*, which is used successfully in this invention, the steps in the following reaction sequence are assumed to occur;

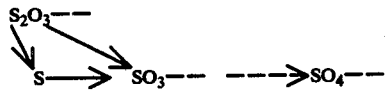

The mechanism of the phenomenon utilized in this invention in which silver is accumulated in the cells of photosynthetic sulfur bacteria is not clear but since silver in waste fix solutions is considered to exist mainly as silver-thiosulfate complex salt of the form of $Na_3Ag(S_2O_3)_2$, it is assumed that the silver or silver compound is captured by the cells of the photosynthetic sulfur bacteria through a course the same as the above-described course of metabolism of $S_2O_3^{--}$.

However, it is difficult to determine which accumulation process predominates under the conditions in practicing the process of this invention and also it is difficult to predict the nature of the accumulated silver or silver salts in relation to the cultivation conditions.

On the other hand, biological activity such as metabolism, growth, and proliferation occurs with photosynthetic sulfur bacteria consuming effectively carbon sources, nitrogen sources and inorganic salts.

A fix solution contains acetates and $CO_3^{--}$ as carbon sources together with inorganic cations such as $Na^+$ and $K^+$ as well as anions such as $Cl^-$, $Br^-$, $I^-$, etc., dissolved therein from silver halides present in silver halide photographic materials. Also, sulfites were found to be very effective for the growth of the photosynthetic sulfur bacteria used in this invention. Ammonium thiosulfate which is generally used in rapid fix solutions contains ammonium ions as a nitrogen source together with thiosulfate ions. Since most of the chemical materials necessary for the biological activity of photosynthetic sulfur bacteria are supplied from a waste fix solution itself, the materials which must be added to the waste fix solution for the biological activity of the bacteria are phosphate ions and small amounts of the salts of iron, magnesium, and calcium only. Trace elements such as cobalt, magnesium, molybdenum, etc., are also required for the growth but a sufficient amount of these materials is generally present in city water.

Since photosynthetic sulfur bacteria are generally autotrophic, Organic materials and vitamins are unnecessary in contrast to other microoganisms. Further since the above — described waste photographic processing solutions are unsuitable for the biological activity of microorganisms other than photographic sulfur bacteria, other reactions of undesirable microorganisms than the desired reaction caused by the comtamination of other undesirable microorganisms do not occur in this invention. The cells of the bacteria after finishing the biological treatment can be easily removed as precipitates by centrigation, by settling the cell suspesion for a certain period of time, by the addition of a protein flocculant, by filtration or by the application of heat treatment, agitation, ultrasonic wave treatment, ultraviolet-light irradiation treatment, X-ray irradiation treatment, a treatment contacting with air or an inert gas, a freezing treatment, treatment by passing electric current therethrough, in which two or more treatments described above can also effectively be employed in combination. A protein flocculant is a chemical substance capable of marked decreasing the solubility or dispersion stability of a protein or cell membrane without influencing the chemical formulation and molecular weight thereof. Suitable protein flocculants include acids, alkalis, urea, guanidine, organic solvents, detergent, heavy metals, trichloroacetic acid, potassium thiocyanate, proteinase, isocyanates, isothiocyanates, aldehydes, active carbons and compounds containing active halogens. These treatments facilitate a reduction in the contamination degree of the waste solution by oxygen consuming compounds originated from the bacteria. Also, it is possible to recover silver from the cells of bacteria containing the silver precipitated and accumulated in the cells.

The feature of purifying waste photographic processing solutions by the process of this invention is applicable to waste photographic processing solutions having higher contents of contaminants as compared with conventional processes using ordinary microorganisms, such as an activated sludge process.

As a decontamination or purifying process of waste solutions by microorganisms, a so-called activated sludge process and other various processes have hitherto been proposed (see Thomas J. Dagon "The Biological Treatment of Photographic Processing Effluents" *Kodak Publication No. J-43*, Eastman Kodak Co., Rochester, N.Y. (1974)) but since in these conventional processes, aerobic microorganisms are usually used and hence an aeration is indispensable for cultivating these microorganisms, the system used for practicing these processes needs additionally pumps for aeration and gas exhaust. On the other hand, when anaerobic bacteria are employed as in the process of this invention, the treatment can be carried out in a closed system, which prevents completely contact of the reaction system with the open air until the treatment is finished, and hence the treatment system does not involve the above described difficulty, i.e., the contamination of undesirable microorganisms into the system.

Another feature of the process of this invention arises because the concentrations of salts and reductive compounds present in waste photographic processing solutions to be treated by the process of this invention may be comparatively higher than those of waste solutions in conventional waste treatments with ordinary microorganisms or bacteria. That is, in an ordinary activated sludge process, the COD value of the waste solutions to be treated must be adjusted to values from about 10 ppm to about 100 ppm, while in the waste treatment with the photosynthetic sulfur bacteria used in the process of this invention, waste solutions having a COD value of up to about tens of thousands ppm can be treated in situ or without need for reducing the COD value and further waste solutions having such a high salt content as about 10 % can be also purified effectively by the process of this invention.

Since, as stated above, the waste photographic processing solution containing contaminants at such a high concentration can be treated as it is according to the process of this invention, the processing tanks and other processing means such as agitators, transporting means, etc., employed in the process of this invention may be small-sized and further, the waste treatment of this invention can be performed using only small amounts of power as compared with the above-described conventional processes. Moreover, since no water or a small amount, if required, of water is necessary for diluting the waste solution prior to the waste treatment in the process of this invention as stated above, water use an be greatly minimized in the process of this invention. Thus, it will be understood that the process of this invention has very large economical advantages.

The conditions employed in performing the treatment of this invention are fundamentally anaerobic conditions but this does not always mean completely oxygen-free conditions in a strict sense or does not always mean that the treatment of this invention must be carried out in a completely closed system and the waste treatment process of this invention can be continuously carried out by appropriately selecting the equipment used.

The process of this invention can be very effectively applied to the purifying of a waste fix solution alone but the process can be more effectively applied to the purifying of a mixture of a waste fix solution and other waste photographic processing solutions, in particular, a waste developer. Moreover, the process of this invention can be applied to not only the purifying of waste photographic processing solutions but also to the purifying of a mixture of a waste solution or solutions formed in the production of photographic materials and a waste fix solution. Still further, the process of this invention is applicable to the purifying of a waste fix solution diluted with water, for example, with washing water for photographic processing.

It is important for the biological activity of the photosynthetic sulfur bacteria for the environmental chemical composition to be suitable for the biological activity for the bacteria and also the hydrogen ion concentration of the environment be in a weakly alkaline region. Since an ordinary waste fix solution itself is weakly acidic, it is necessary to adjust the pH of the waste fix solution using $NaHCO_3$, etc., prior to the cultivation treatment when such a waste solution is treated alone but since a waste developer is alkaline, the pH of the waste fix solution to be treated can be easily adjusted to a pH range of about 7 to about 8 suitable for the biological activity of the phtosynthetic sulfur bacteria by adding a waste developer thereto.

Another advantage of adding a waste developer to a waste fix solution is that the developing agent present in the waste developer is a weak reducing agent and hence there is a possibility that the developing agent acts as a proton donor. Still another advantage of this invention is to provide an environment containing sodium sulfite in a large amount which is very effective for maintaining the reaction system in a reductive state, that is, under anaerobic conditions and very advantageous for the biological activity of the photosynthetic sulfur bacteria.

It is known that the silver-thiosulfate complex salt present in a waste fix solution forms various types of complex salts depending upon changes in pH value and ionic strength but it is considered that under ordinary conditions, $Ag(S_2O_3)_2^{---}$ predominates as the complex salt. It is known that $Ag^+$ is very harmful to normal biological activity of microorganisms and bacteria but the influence of the silver-thiosulfate complex salt on the metabolism of bacteria has not been clarified.

Since as stated before, silver itself is a very valuable and expensive metal, various efforts have been made for recovering silver from photographic processing effluents. Therefore, the silver ion concentration in the waste fix solution to be treated further with biological processes is usually quite low and in such a case the presence of silver in the waste solution does not decisively hinder the growth of bacteria.

On the other hand, as the result of investigating a silver recovery treatment where treatment prior to the bacteria treatment of waste fix solutions has not been employed, that is, the case in which waste solutions containing a large amount of silver are used, the following has been found.

That is, silver complex salts are captured by the cells of bacteria during biological activity such as growth, metabolism, etc. Metabolism of the cells of the bacteria in which a large amount of silver ions have been captured stops and the cells precipitate and accumulate on the bottom of the incubator. The concentration of silver-complex salt completely hindering the browth of bacteria depends on the kind and concentration of the bacteria and the relative concentration of the silver complex salt and the bacteria. For example, it has been confirmed that when a solution containing 3% by weight silver complex salt is inoculated with photosynthetic sulfur bacteria in an optimal growth concentration and the system is continuously irradiated with light, the cells of the bacteria in which a large amount of silver salt has been captured precipitate and accumulate but the cells of the bacteria containing a small amount of silver salt continue normal growth and proliferate and finally containing the normal cells of bacteria in a stationary state is obtained. Of course, by freshly adding innoculum separately grown under anoptimal conditions for growth, which are given in Example 1 to the waste solution appropriately, the growth and the proliferation of the bacteria, that is, the purifying of the waste solution can be more easily practiced.

This invention is based on the discovery that when photosynthetic sulfur bacteria are cultivated in a waste fix solution, the silver-thiosulfate complex salts in the solution are captured by the cells of the bacteria and accumulate in the cells of the bacteria as insoluble metal or salts. It has also been found that the amount and the rate of the silver or silver salts captured by the cells of the bacteria differ according to the concentration of the cells of the bacteria and the silver salts, the amount of light irradiated, the composition and the pH of the culture solution, etc., but it is easily possible to achieve a total amount of silver accumulated in the cells of the bacteria of about 10 to about 20% by weight of the total dry weight of the cells, while the final silver concentration in the waste solution cultivated at a low concentration of the silver complex salts could be reduced as low as 0.1 ppm.

In the process of this invention, by appropriately selecting the amount of the cells of photosynthetic sulfur bacteria, silver can be directly accumulated in the cells of the bacteria from the waste fix solution. For attaining such growing conditions, it is appropriate to add to the waste fix solution salts necessary for the growth of the bacteria using city water as a diluent, general municipal sewage, washing water used for photographic processing, a waste developer, or a waste solution previously subjected to the bacterial treatment.

Processes of separating silver from the cells of the bacteria, include a process wherein organic materials are removed by incineration and a process wherein the cells of the bacteria having silver captured therein are treated with a solution containing a surface active agent, strong alkali or acid, a bacteriophage, or proteolytic enzyme to disolve the cells of the bacteria and precipitate sparing soluble silver and/or silver salts, which are recovered and purified. More specifically, highly active surface active agents which destroy or solubilize cell membranes are suitable for recovering silver. Anionic surfactants such as sodium dodecyl sulfate, sodium dodecyl benzene sulfonate etc. or cationic surfactants such as lauryl ammonium chloride, lauryl dimethyl amine oxide etc. are suitable examples of surface active agents which can be employed.

Also an alkaline solution or an acid solution can also be used as a good disintegrator of the bacterial cells for silver recovery. Further, bacteriophages or lysozymes which destroy cell walls of bacteria can be used to solubilize the bacteria and separate the granular silver from the bacteria.

As set forth hereinbefore, the term, photosynthetic sulfur bacteria, is used to describe microorganisms which are phototrophic and able to metabolize inorganic sulfur compounds, or more specifically they can be defined as microorganisms which are able to grow as anaerobes or aerotolerate in the light in mineral media containing inorganic sulfur compounds, bicarbonate and some simple organic substrates. Generally no organic growth factors are required but some species require Vitamin $B_{12}$.

Detailed descriptions of these organisms can be found in the following reference *Bergey's Manual of Determinative Bacteriology*, R. E. Buchanan and N. E. Gibbons, Coeditors, 8th Edition, pp 34–61, The Williams and Wilkins Company, Publisher, Baltimore U.S.A., (1974).

According to this reference phototropic sulfur bacteria (or photosynthetic, as used herein) can be classified into two families; *Chromatiaceae* and *Chlorobiaceae*. Some of these species are stored at ATCC (American Type Culture Collection) or SMG (Sammlung für Mikroorganismen Göttingen) and can be obtained therefrom. Their accession numbers are written below to the right of the specie names.

| I. Genus *Chromatium* | |
|---|---|
| 1. *Chromatium okenii* | SMG 169 |
| 2. *Chromatium weissei* | SMG 171 |
| 3. *Chromatium wermingii* | SMG 173, ATCC 14959 |
| 4. *Chromatium buderi* | SMG 176, ATCC 25588 |
| 5. *Chromatium minus* | SMG 178 |
| 6. *Chromatium biolascens* | SMG 198, ATCC 17096 |
| 7. *Chromatium vinosum* | ATCC 17899 |
| 8. *Chromatium gracile* | SMG 203 |
| 9. *Chromatium minutissimum* | |
| II. Genus *Thiocystis* | |
| 1. *Thiocystis violacea* | SMG 207 |
| 2. *Thiocystis gelatinosa* | SMG 215 |
| III. Genus *Thiosarcina* | |
| IV. Genus *Thiospirillum* | |
| 1. *Thiospirillum sanguineum* | |
| 2. *Thiospirillum jenense* | SMG 216 |
| 3. *Thiospirillum rosenbergii* | |
| V. Genus *Thiocapsa* | |
| 1. *Thiocapsa roseopersicina* | SMG 217 |
| 2. *Thiocapsa pfennigii* | |
| VI. Genus *Lamprocystis* | |
| VII. Genus *Thiodictyon* | |
| 1. *Thiodictyon elegans* | SMG 232 |
| 2. *Thiodictyon bacillosum* | SMG 234 |
| VIII. Genus *Thiopedia* | |
| IX. Genus *Amoebobacter* | |
| 1. *Amoebobacter roseus* | SMG 235 |
| 2. *Amoebobactor pendens* | SMG 236 |
| X. Genus *Ectothiorhodospira* | |
| 1. *Ectothiorhodospira mobilis* | SMG 237 |
| 2. *Ectothiorhodospira shaposhnikovii* | SMG 243 |
| 3. *Ectothiorhodospira halophila* | SMG 244 |
| Family *Chlorobiaceae* is classified as follows; | |
| I. Genus *Chlorobium* | |
| 1. *Chlorobium limicola* | SMG 245 |
| 1a. *Chlorobium limicola* forma sp. *thiosulfatophilum* | SMG 249 |
| 2. *Chlorobium vibrioforme* | SMG 260 |
| 2a. *Chlorobium vibrioforme* forma sp. *thiosulfatophilum* | SMG 265 |
| 3. *Chlorobium phaeobacteroides* | SMG 266 |
| 4. *Chlorobium phaeovibrioides* | SMG 269 |
| II. Genus *Prosthecochlis* | SMG 271 |
| III Genus *Chloropseudomonas* | |
| IV. Genus *Pelodictyon* | |
| 1. *Pelodictyon clathratiforme* | |
| 2. *Pelodictyon luteolum* | SMG 273 |
| V. Genus *Clathrochloris* | |

These photosynthetic sulfur bacteria identified are given only to aid in a better understanding of the invention, since these species are those that are purified and identified bacteria among many unidentified species. It should be understood that for the embodiment of this invention, it is not necessary to use purified and well identified species and in many cases a mixture of unidentified microorganisms gives excellent results.

All of these species can utilize inorganic sulfides as an electron donor. Therefore, they can be used in this invention as in the following manner.

1. Addition of sodium sulfide to a waste fix solution in order to form $Ag_2S$ and recover it as precipitate.
2. Treatment of the waste fix solution which contain excess sulfide but low concentration of silver with photosynthetic bacteria in order to oxidize sulfide ions into sulfate and accumulate silver within the bacterial cells.

However the invention can be applied more successfully when photosynthetic bacteria can utilize thiosulfate. By utilizing these photosynthetic sulfur bacteria, a waste fix solution which contains a high concentration of thiosulfate can be treated directly. Among the photosynthetic sulfur bacteria listed above, the followings are suitable for this purpose since they can metabolize thiosulfate as well as sulfide.

| I. Family *Chromatiaceae*: | |
|---|---|
| 1. The following species of Genus *Chromatium*: | |
| *Chromatium violacens* | ATCC 17096 |
| *Chromatium vinosum* | ATCC 17899 |
| *Chromatium gracile*, and | |
| *Chromatium minutissimum* | |
| 2. The following species of Genus *Thiocystis*: | |
| *Thiocystis violacea* | SMG 207 |
| 3. The following species of Genus *Thiocapsa*: | |
| *Thiocapsa pfennigii* | |
| 4. The following species of Genus *Amoebobacter*: | |
| *Amoebobacter rosens* and | |
| *Amoebobacter pendens* | SMG 236 |
| 5. The following species of Genus *Ectothiorhodospira*: | |
| *Ectothiorhodospira mobils* | SMG 237 |
| *Ectothiorhodospira shaposhnikovii* and | SMG 243 |
| *Ectothiorhodospira halophila* | SMG 244 |
| II. Family *Chlorobiaceae*: | |
| 1. The following species of Genus *Chlorobium*: | |
| *Chlorobium limicola* forma sp. *thiosulfatophilumi*, | SMG 249 |
| and *Chlorobium vibrioforme* forma sp. *thiosulfatophilum* | SMG 265 |
| 2. The following species of Genus *Chloropseudomonas*: | |
| *Chloropseudomonas ethylica*. | |

Of the above-described photosynthetic sulfur bacteria, *Chromatium vinosum* is particularly suitable for attaining the objects of this invention since the bacterium can grow under various environmental conditions and compositions in respect to temperature, pH, salts, organic materials, etc., it weeds out other undesirable bacteria if they enter the system, and it captures thiosulfate ions well.

The temperatures at which the biological activity of the photosynthetic sulfur bacteria can occur differ greatly and can range from about 0° C to about 90° C depending on the kind of species employed but the process of this invention can be effectively practiced at a temperature ranging from about 5° C to about 55° C, and further a temperature ranging from about 20° C to about 35° C centering around 30° C is more preferable in this invention. At temperatures outside the above-described temperature ranges, the biological activity of the bacteria is only that activity required for the bacteria to stay alive and the rate of metabolism of the sulfur compounds in the bacteria becomes very low, which results in reducing the effect of this invention.

The wavelength regions of the light that the photosynthetic sulfur bacteria used in this invention utilize for photosynthesis are those of near ultraviolet light, visible light, and near infrared light of from about 300 nm to about 1200 nm. It is preferred for the light utilized in this invention to have a continuous spectral distribution in the wavelength region. A particularly preferred light is light having a continuous spectral distribution in the wavelength region of from about 350 nm to about 100 nm. Light in the above-described wavelength region is absorbed by either of bacteriochlorophyll or auxiliary pigment (e.g., caroteniods, flavins, etc.,). Typical examples of light sources providing the above-described wavelength and spectral distibution characteristics are sun light, a tungsten incandenscent lamp, a halogen-containing tungsten incandescent lamp, a xenon discharge lamp, an arc discharge lamp, etc., and the process of this invention shows remarkable effects in employing such light sources. However, a light source having line spectra and continuous spectra, such as a fluorescent lamp may be used in this invention although in this case the effect of the process of this invention is reduced to some extent. Furthermore, irradiation with a combination of lights with wavelengths which are absorbable by the above-described pigments, can be employed in the process of this invention.

In the process of this invention, the energy density of the light used for radiation is above about 1/$\mu$watt/cm$^2$, preferably from about 100 $\mu$watts/cm$^2$ to about 1 watt/cm$^2$. If the energy density of the light irradiated is lower than about 1 $\mu$watt/cm$^2$, the rate of oxidizing sulfur compounds by the photosynthetic sulfur bacteria is reduced, while if the energy of light irradiated is too high, the pigments in the bacteria are sometimes bleached. Thus, light energy densities outside the above-described range can be employed but, desirable effects are attained by the process of this invention only when light energy densities within the above described range are used.

The process of this invention may be carried out in practice by a batch system or using a continuous reaction system. In order to grow the photosynthetic sulfur bacteria well, anaerobic conditions must be used but the extent of oxygen removal depends upon the kind of the bacteria and the cultivation conditions. For example, *Chromatium vinosum* has a comparatively high oxygen resistance and the existence of a small amount of oxygen in the system does not hinder the growth of the bacteria when this bacterium is employed as the photosynthetic sulfur bacteria.

In either the batch system and the continuous system, the removal efficiency of silver from a waste fix solution containing the silver complex salt depends largely on the number of cells of bacteria, the concentration of the silver complex salt, and the treatment conditions. However, by returning the waste solution initially subjected to the silver removal treatment by the photosynthetic sulfur bacteria to the reaction tank again or by adding fresh photosynthetic sulfur bacteria inoculated separately to the waste solution, silver in the waste fix solution can be concentrated and recovered at a yield of substantially 100%.

The process of purifying photographic processing effluents and the process of recovering silver therefrom using the photosynthetic sulfur bacteria were described above in regard to the principles and the features of this invention and further to the principles and the features of this invention and further the process of this invention is described in greater detail by reference to the following examples. Unless otherwise indicated herein, all parts, ratios and the like are by weight.

EXAMPLE 1

One liter of a culture solution prepared by adding to Standard Solution (I) having the composition shown below 2 g of sodium thiosulfate and 1 g of sodium sulfide was inoculated with purple photosynthetic sulfur bacteria, *Chromium vinsum*, in a transparent glass bottle with a stopper and was continuously irradiated with light from a tungsten incandescent lamp at a mean light intensity of about 2 milli watts/cm$^2$ in a water bath maintained at 30° C.

| Composition of Standard Solution (I): | |
|---|---|
| NaCl | 30 g |
| NH$_4$Cl | 1.0 g |
| KH$_2$PO$_4$ | 0.5 g |
| K$_2$HPO$_4$ | 0.5 g |
| MgCl$_2$ . 6H$_2$O | 0.5 g |
| CaCl$_2$ | 0.05 g |
| FeCl$_3$ . 6H$_2$O | 0.005 g |
| NaHCO$_3$ | 2.0 g |

-continued

| Composition of Standard Solution (I): | |
|---|---|
| City water to make | 1 liter |

After 3 days of light irradiation, the concentration of the cells of the bacteria reached a stationary state. The optical density of the culture suspension thus formed was 0.9 when checked at 373 nm (hereinafter, this optical density is referred to as OD$_{373}$). The cells of the bacteria were recovered from the suspension by centrifugal separation for 10 minutes at 5,000 X/g and was redispersed in 100 ml of Standard Solution (I) (not containing sodium thiosulfate and sodium sulfide) to provide a concentrated cell suspension.

EXAMPLE 2

A solution prepared by adding 2.0 g of Na$_2$S$_2$.S$_3$·5H$_2$O to 245 ml of Standard Solution (I) as described in Example 1 was inoculated with 5 ml of the concentrated cells suspension prepared in the same manner as in Example 1 in a 250 milliliter transparent narrow-mouthed reagent bottle to provide a solution having and OD$_{373}$ of 0.25. The solution thus prepared was irradiated with light from a tungsten incandescent lamp at a light intensity of 1.1 milli watts/cm$^2$ for 3 days at room temperature (about 20°– 30° C), subjected then to centrifugal separation for 10 minutes at 5,000 X/g. The concentration of S$_2$O$_3$—— in the supernatant liquid was determined by a titration with a 0.05 N KI—I$_2$ solution. As a control sample, a solution prepared by diluting and treating at the same conditions as above but without light irradiation was subjected to centrifugal separation and the concentration of S$_2$O$_3$ ——in the supernatant liquid was also measured. The result showed that the concentration in the control sample was 6,700 ppm as Na$_2$S$_2$O$_3$, while that of the solution subjected to the treatment of this invention was 530 ppm. Thus, the above result shows that about 92% of thiosulfate ions were oxidized by the bacterial treatment of this invention.

EXAMPLE 3

In 200 ml of a standard culture medium having the same composition as that of Standard Solution (I) shown in Example 1 contained in a 250 milliliter transparent narrowmouthed reagent bottle were dissolved 0.25 g of Na$_2$S·9H$_2$O and 0.5 g of Na$_2$S$_2$O$_3$ and the solution was inoculated with 5 ml of a solution of the cells of the bacteria at a stationary concentration state prepared as in Example 1. The cultivation was carried out for one week at room temperature under the irradiation of light from a tungsten incandescent electric lamp at a light intensity of 1.1 milli watts/cm$^2$.

When the concentration of the culture suspension reached a stationary state, the culture solution thus treated was subjected to centrifugal separation for 10 minutes at 5,000 X/g and the COD value of the supernatant liquid was measured using a COD meter, HC-107 made by Central Kagaku K.K. according to the methods of JIS K-0101 and JIS K-0120.

As a control test, the above-described culture solution was subjected to centrifugal separation without being subjected to the bacterial treatment of this invention and the COD value of the supernatant liquid was also measured in the same manner as above.

The COD value in the control case was 2,400 ppm, while that of the culture solution subjected to the bacterial treatment of this invention was 31 ppm. The above result shows that the COD value of the solution was reduced by the bacterial treatment of this invention to 1.3% of the solution prior to the treatment.

EXAMPLE 4

A waste fix solution containing a large amount of silver complex salts used for the fix treatment of X-ray photographic materials for commercial use was diluted 100 times with city water and after adjusting the pH of the solution to 8.0 by adding sodium hydrogencarbonate, and to 225 ml of the thus obtained diluted waste fix solution 25 ml of a concentrated solution of the cells of the bacteria prepared as in Example 1 was added. The mixture was cultivated under irradiation with light as in Example 2.

Since silver ions were captured in the cells of the bacteria and a large part of the cells were precipitated, 5 ml of the concentrated cell suspension was freshly added to the system followed by continuation of the cultivation for 3 additional days. Thereafter, the COD value of the system was measured in the same manner as described in Example 3. As a control, the COD value of the waste fix solution which was not subjected to the bacterial treatment of this invention was measured.

The COD value in the control was 1,800 ppm, while that of the solution subjected to the bacterial treatment of this invention was 90 ppm. The result shows that the COD value of the waste fix solution was reduced to 5% thereof by the bacterial treatment of this invention.

EXAMPLE 5

To 50 ml of the waste fix solution as used in Example 4 was added dropwise gradually 5 ml of a 2.5 N aqueous $Na_2S$ solution to precipitate $Ag_2S$, which was removed from the solution by filtration with a filter paper. The supernatant liquid thus obtained was adjusted to a pH of 8 with sodium hydrogencarbonate. To 245 ml of the supernatant liquid thus adjusted was added 5 ml of a concentrated cell suspension prepared in the same manner as in Example 1 and after carrying out the cultivation of one week under conditions as in Example 2, the cells of the bacteria were removed from the culture suspension by centrifugal separation for 10 min at 5,000 X/g as in Example 2 and the COD value of the supernatant liquid was measured in the same manner as in Example 3. Also, as a control, the COD value of the solution prior to the addition of the cells of the bacteria was measured.

The COD value of the control was 1,600 ppm, while that of the culture solution was 38 ppm.

The result shows that 98% of the reductive materials in the waste fix solution were oxidized by the bacterial treatment of this invention.

EXAMPLE 6

A mixture of a waste developer and a waste fix solution used for processing color photographic silver halide photosensitive materials by means of an automatic developing machine was diluted 20 times with Standard Solution (I) as described in Example 1. The pH of the solution mixture was 8.1 and a small amount of white precipitate formed.

To 225 ml of the solution mixture was added 25 ml of a solution of the cells of the bacteria prepared as in Example 1 and after cultivating for 4 days under irradiation of light as in Example 2, the $BOD_5$ (the BOD value after the cultivation of 5 days) and the COD of the culture solution were measured according to the methods of JIS K-0101 and JIS K-0102. As a control, the same indices of the solution mixture prior to the addition of the cells of the bacteria were measured.

The $BOD_5$ value for the control was 3,700 ppm, while that of the solution subjected to the bacterial treatment of this invention was 580 ppm. The result shows that the oxygen demand was reduced to about 17% of the original value by the treatment of this invention. Also, the COD value for the control was 8,440 ppm, while that of the solution subjected to the bacterial treatment of this invention was 1,540 ppm. This result shows that the oxygen demand was reduced to 18% of the control by the treatment of this invention.

EXAMPLE 7

A 0.4 M solution of a silver-thiosulfate complex salt ($Na_3Ag(S_2O_3)_2$) was prepared by dissolving silver chloride in an aqueous solution of sodium thiosulfate in the dark. In a 120 milliliter transparent narrow-mouthed bottle were placed 25 ml of Standard Solution (I) as described in Example 1 and 90 ml of the 0.4 M solution of the silver-thiosulfate complex salt prepared above and after adding 5 ml of concentrated cell suspension prepared in the manner as in Example 1 to the mixture in the bottle, cultivation was performed for 3 days at room temperature under irradiation of light from a tungsten lamp at an intensity of 1.1 milli watt/cm$^2$.

By the treatment, the cells of the bacteria largely blackened and precipitated. The precipitate was recovered, redispersed in 300 ml of water, and the suspension was subjected to centrifugal separation for 10 minutes at 4,000 X/g followed by washing. After repeating the same centrifugal separation and washing twice, the precipitate thus recovered was dried, weighed, and the total amount thereof was dissolved in concentrated nitric acid. After diluting the solution, the amount of silver in the solution thus prepared was measured using atomic absorption analysis. The amount of silver in the cells of the bacteria in the solution cultivated in the solution was 15% as a dry weight ratio of the weight of the cells.

EXAMPLE 8

The same procedure as Example 7 was followed using, in this case 30 ml of the 0.4 M solution of the silver-thiosulfate complex salt and 85 ml of Standard Solution (I) described in Example 1 and the amount of silver in the cells of the bacteria thus cultivated was measured. The amount of the silver in the cells was 6.5% as a dry weight ratio.

EXAMPLE 9

A waste fix solution collected from an automatic developing machine for X-ray photographic films for commercial use was added to Standard Solution (I) as described in Example 1 at a concentration of 5% and 245 ml of the culture solution thus prepared was placed on a 250 milliliter transparent narrow-mouthed bottle. Then, after adding thereto 5 ml of concentrated cell suspension prepared in the manner as described in Example 1, the cultivation was carried out for 3 days.

The cells of the bacteria were blackened and precipitated. The precipitate was recovered, redispersed in 300 ml of water, and the precipitate was recovered from the dispersion by a centrifugal separation for 10 minutes at 4,000 X/g. The same centrifugal separation and washing were repeated twice.

The precipitate thus recovered was dispersed in 20 ml of a solution containing 5% gelatin as a binder and coated on a glass plate of 78 cm² and then the amount of silver on the plate was quantitatively analyzed using a X-ray fluorescence analysis.

As a comparison, the silver-containing waste fix solution in which the cells of the bacteria were not cultivated was coated on a plate together with 5% gelatin and the amount of silver was measured in the same way as above. The result showed that about 30% of the total silver in the solution subjected to the cultivation treatment of this invention was captured in the cells of the bacteria.

EXAMPLE 10

To a mixture of 2.5 ml of the waste fix solution as in Example 9 and 242.5 ml of Standard Solution (I) as described in Example I was added 5 ml of a concentrated solution of the cells of the bacteria as in Example 1 to make a total solution mixture of 250 ml and then the bacteria was cultivated for 2 days as in Example 9.

Then, the cells of the bacteria were recovered from the culture solution by subjecting the solution to centrifugal separation for 10 minutes at 4,000 X/g, redispersed in 300 ml of city water, subjected to centrifugal separation, and then washed twice. The total amount of the precipitate was dispersed in 20 ml of a solution containing 5% gelatin and the dispersion was coated on a glass plate of 78 cm² followed by drying. Then, the amount of silver was quantitatively analyzed using a X-ray fluorescence analysis.

As a comparison, a mixture of 0.25 ml of the waste fix solution and 20 ml of the solution containing 5% gelatin was coated on a glass plate and the amount of silver was measured in the same manner as above.

The amount of silver in the comparison was 7 $\mu g/cm^2$, while the amount of silver contained in the sample of this invention was 56.4 $\mu g/cm^2$. The result shows that 80% of the amount of silver contained in the culture solution was accumulated in the cells of the bacteria and recovered by the process of this invention.

EXAMPLE 11

The same procedure as in Example 10 was followed using, in this case, a mixture of 2.5 ml of the waste fix solution and 2.5 ml of a waste developer recovered from an automatic X-ray processor for commercial use as the culture solution.

After cultivation for 2 days, the cells of the bacteria were recovered as in Example 10, washed with water, coated on a glass plate using a gelatin solution as described above, and then the amount of silver was measured.

As a comparison, the above mixture was dispersed in a solution containing 5% gelatin and the dispersion coated on a glass plate. The amount of silver was measured as in Example 10.

The amount of silver in the comparison test was 7 $\mu g/cm^2$, while the amount of silver in the cells of the bacteria cultivated as above was 67 $\mu g/cm^2$. The result shows that 96% of the amount of silver contained in the culture solution was accumulated in the cells of the bacteria and recovered by the process of this invention.

EXAMPLE 12

In the procedure as in Example 10, 10 ml of a waste fix solution and 10 ml of a waste developer recovered from an automatic processor for commercial use employed for developing and fixing lithographic photosensitive materials were mixed with 210 ml of Standard Solution (I) as described in Example 1 and after adding thereto 20 ml of a concentrated cell suspension as prepared in Example 1, the mixture was placed in a 250 milliliter transparent narrow-mouthed bottle followed by cultivation for 2 days as in Example 9.

After the cultivation for 2 days, the cells of the bacteria were recovered as in Example 10, washed with water, mixed with a gelatin solution and then coated on a glass plate, and the amount of silver was measured.

As a comparison, a gelatin solution containing 10 ml of the waste fix solution prior to the bacterial treatment was coated on a glass plate having the same area as above and the amount of silver was measured. Furthermore, as another comparison, a gelatin solution containing 10 ml of the super-natant liquid obtained in the above procedure of this invention after removing the cells was also coated on a glass plate and the amount of silver was measured.

The amount of silver in the sample prepared by coating the cells of the bacteria on the glass plate was 212 $\mu g/cm^2$, while the amount of silver in the sample prepared by coating the waste fix solution which was not subjected to the bacterial treatment was 259 $\mu g/cm^2$. Also, the amount of silver of the sample prepared by coating the supernatant liquid formed by removing the cells of the bacteria was 0.9 $\mu g/cm^2$. The result shows that 82% of silver contained in the culture solution was accumulated in the cells of the bacteria and recovered.

EXAMPLE 13

To 1.75 liters of a solution of *Chromatium vinosum* at a stationary concentration state prepared as in Example 1 contained in a two liter narrow-mouthed bottle was added 250 ml of a solution prepared by diluting 10 times a waste fix solution recovered from an automatic processor for X-ray films and adjusting the pH thereof to 7.0 with $NaHCO_3$ and the cells of the bacteria were cultivated in the bottle under the irradiation of light.

Before starting the cultivation, 50 ml of the culture solution was sampled and after filtering away the cells of the bacteria using a Fuji Microfilter FM 120 (made by Fuji Photo Film Co., Ltd.), the amount of silver in the filtrate was measured using an atomic absorption method. The amount of silver was 325 mg/liter. The dry weight of the cells of the bacteria collected on a filter paper was 10.3 mg.

After continuing the cultivation under the irradiation of light, the cells of the bacteria were removed as in the above procedure and the amount of silver in the filtrate was measured. The amount of silver was 5.3 mg/liter. The dry weight of the cells of the bacteria was 13.7 mg. Also, after continuing the cultivation for 2 days, the amount of silver in the filtrate was 3.3 mg/liter and the dry weight of the cells of the bacteria was 14.0 mg. About 90% of silver in the solution was removed by the bacterial treatment.

EXAMPLE 14

An apparatus for continuous cultivation was prepared using an 8 liter-cylindrical cultivation tank made of a transparent plastic and having a diameter of 18 cm and height of 28 cm. A culture solution prepared by adding sodium thiosulfate to Standard Solution (I) as described in Example 1 at a rate of 2.0 g/liter was stored in a supply tank, the COD value of this culture solution being 586 mg/liter. Then, *Chromatium vinosum* was continuously cultivated while supplying the culture solution to the cultivation tank at a rate of 1 liter/day. After continuing the cultivation for 5 days, a culture solution having almost a constant concentration of the cells of the bacteria was obtained. From the solution discharged, 100 ml of the solution was sampled and the cells of the bacteria were removed by filtering with a Fuji Microfilter FM 120 to provide a transparent filtrate. The COD value of the filtrate was 195 ppm.

After 7 days of continuous cultivation under light irradiation, a solution prepared by adding 0.5 g/liter of $KH_2PO_4$ and 1 g/liter of $NaHCO_3$ to the effluents discharged from automatic processors for color films and color papers was continuously supplied to the system at a rate of 1 liter/day. The COD value of the solution supplied was 260 mg/liter and the content of silver was 6.2 mg/liter. After continuing the continuous cultivation for 2 days, a solution discharged from the apparatus was sampled. The bacterial cells were removed by filtration as in Example 13 and the COD value in the solution thus formed was measured. The value was 83 mg/liter. At the same time the silver content of the same solution was determined by an atomic absorption method. The content of silver in the solution was 0.07 mg/liter.

EXAMPLE 15

A waste fix solution from an automatic processor for lithgraphic films was treated with *Chromatium vinosum* under the same conditions described in Example 13. The bacterial cells recovered by centrifugation were dispersed in 50 ml of 0.1 N sodium hydroxide solution and then the suspension was boiled for 10 min. Most of the bacterial cells were dissolved. The suspension was centrifuged for 5 min at 500 x/g and the supernatant was discarded. Metallic crystal layers were collected at the bottom of the tube together with some cell debris on top of the crystals. An X-ray diffraction analysis of the precipitates confirmed that these crystals consisted mainly of metallic silver.

EXAMPLE 16

A waste fix solution from an automatic processor for X-ray films was treated with *Chromatium vinosum* in the same manner described in Example 13. The bacterial cells recovered by centrifugation were dispersed in 20 ml of solution containing 1% sodium dodecyl sulfate in a glass tube and then the suspension was subjected to an ultrasonic cell homogenizer for 5 min. The suspension was centrifuged for 5 min at 500 X/g and the supernatant was discarded. Metallic silver crystals were recovered from the precipitation. The size of the silver crystals were found to range from 200 to 2000 A using electronmicroscopic observation. The silver concentration of the precipitate was 63% on a dry basis.

While the invention was been described in detail and with reference to specific embodiments thereof, it will be apparent to one skilled in the art that various changes and modifications can be made therein without departing from the spirit and scope thereof.

What is claimed is:

1. A process for recovering silver from and purifying a waste fixing solution used for the fixing of a silver-halide photographic material containing at least one silver-thiosulfate complex salt which comprises applying photosynthetic sulfur bacteria to the waste fixing solution, under substantially anaerobic conditions with irradiation of light, cultivating the cells of the bacteria to concentrate and accumulate silver in the waste solution into the cells of the bacteria as silver metal or insoluble silver salts, recovering the cells of the bacteria and separating silver or silver salts from the cells.

2. The process as described in claim 1, wherein the process includes admixing a dispersion of cells of photosynthetic sulfur bacteria with the wate fixing solution.

3. The process as described in claim 1, wherein said waste fixing solution is a waste fixing solution diluted with water.

4. The process as described in claim 3, wherein aid waste fixing solution is a waste fixing solution diluted with water to an extent more than two times the amount by volume of water to the volume of the fixing solution.

5. The process as described in claim 1, wherein said waste fixing solution is a mixture of a waste fixing solution and another waste photographic processing solution or solutions.

6. The process as described in claim 1, wherein said waste fixing solution is a mixture of a waste fixing solution, another photographic processing solution or solutions, and water.

7. The process as described in claim 5, wherein said other photographic processing solution is a waste photographic developer.

8. The process as described in claim 6, wherein said other photographic processing solution is a waste photographic developer.

9. The process as described in claim 1, wherein said photosynthetic sulfur bacteria are bacteria of the Family *Chromotiaceae*.

10. The process as described in claim 1, wherein said photosynthetic sulfur bacteria are bacteria of the Genus *Chromatium* and which are able to metabolize thiosulfate.

11. The process as described in claim 1, wherein said photosynthetic bacteria are *Chromatium vinosum*.

12. The process as described in claim 1, wherein the application of the photosynthetic sulfur bacteria is performed by placing said bacteria in the waste fixing solution to permit the biological activity of the bacteria to occur.

13. The process as described in claim 1, wherein the irradiation with light is irradiation with light in the near ultraviolet region, visible region, or near infrared region having a wavelength ranging from about 300 nm to about 1200 nm.

14. The process as described in claim 13 wherein the intensity of light irradiated is above about 1 $\mu watt/cm^2$.

15. The process as described in claim 1 wherein the cultivating of the bacteria in the waste fixing solution is at a temperature of from about 5° C to about 55° C.

16. The process as described in claim 1, wherein the pH of said fixing solution ranges from about 5 to about 10.

17. The process as described in claim 1, wherein the recovered cells of the bacteria are incinerated, thereby silver or silver salts is separated from the cells.

18. The process as described in claim 1, wherein the recovered cells of the bacteria are treated with a solution containing a surface active agent, a strong alkali or an acid, a bacteriophage, or proteolytic enzyme, to dissolve the cells and to separate the silver or silver salts from the cells.

* * * * *